US 9,052,325 B2

(12) United States Patent
Halverson

(10) Patent No.: US 9,052,325 B2
(45) Date of Patent: *Jun. 9, 2015

(54) SYSTEMS AND METHODS FOR DETERMINING ANTIBODY-MEDIATED RISK INDEX

(71) Applicant: NEW YORK BLOOD CENTER, INC., New York, NY (US)

(72) Inventor: Gregory R. Halverson, New York, NY (US)

(73) Assignee: NEW YORK BLOOD CENTER, INC., New York, NY (US)

(*) Notice: Subject to any disclaimer, the term of this patent is extended or adjusted under 35 U.S.C. 154(b) by 36 days.

This patent is subject to a terminal disclaimer.

(21) Appl. No.: 13/837,390

(22) Filed: Mar. 15, 2013

(65) Prior Publication Data
US 2013/0203090 A1    Aug. 8, 2013

Related U.S. Application Data

(63) Continuation-in-part of application No. 12/908,770, filed on Oct. 20, 2010, now Pat. No. 8,426,210.

(60) Provisional application No. 61/253,774, filed on Oct. 21, 2009.

(51) Int. Cl.
    *G01N 33/68* (2006.01)

(52) U.S. Cl.
    CPC ........ *G01N 33/6854* (2013.01); *G01N 2800/22* (2013.01); *G01N 2800/245* (2013.01)

(58) Field of Classification Search
    USPC ............. 436/507, 513, 517, 522, 523, 10, 67, 436/69, 811; 435/7.1, 7.2, 7.24, 7.25, 69.6, 435/334, 337
    See application file for complete search history.

(56) References Cited

U.S. PATENT DOCUMENTS

8,426,210 B2 * 4/2013 Halverson ................ 436/67
2010/0261203 A1 * 10/2010 Cicciarelli et al. ........ 435/7.21

FOREIGN PATENT DOCUMENTS

WO    2011/050172 A1    4/2011

OTHER PUBLICATIONS

Malcata et al. RBC and HLA Immunization in blood donors at the Lisbon Regional Blood Centre, Vox Sanguinis 101 (Suppl 1): p. 288 Abstract P-519 (Jul. 2011).*
Kjeldsen-Kragh et al. Challenges in testing for platelet-related adverse events, Vox Sanguinis 101 (Suppl 1): p. 24 Abstract 3C-S6-01 (Jul. 2011).*
Cruz et al. Transfusion-related acute lung injury: a thrombotic thrombocytopenic purpura treatment-associated case report, Journal of Clinical Apharsis 23 (2): 96-103 (2008) (Abstract Only).*
Zupanska Assays to predict the clinical significance of blood group antibodies, Current Opinion in Hematology 5: 412-416 (1998).*

(Continued)

*Primary Examiner* — Gail R Gabel
(74) *Attorney, Agent, or Firm* — K&L Gates LLP; Louis C. Cullman; Michelle Glasky Bergman

(57) ABSTRACT

Systems and methods are provided for assessing the risk of hemolytic disease of the fetus or neonate, neonatal alloimmune thrombocytopenic purpura, or transfusion-associated lung injury in a patient or transfusion recipient.

19 Claims, 3 Drawing Sheets

(56) References Cited

OTHER PUBLICATIONS von Allmen et al. Development of a C1q-ABO-ELISA to measure C1q binding by human anti-A alloantibodies. J. Immunol. Methods 171 (1): 85-92(May 2, 1994).*

Arndt et al. "A retrospective analysis of the value of monocyte monolayer assay results for predicting the clinical significance of blood group alloantibodies." Transfusion, Sep. 2004, vol. 44, No. 9, pp. 1273-1281.

Fabron Jr. et al. "Application of noninvasive phagocytic cellular assays using autologous monocytes to assess red call alloantibodies in sickle cell patients." Transfusion and Aphereisis Science: Official Journal of the European Society for Haemapheresis, Aug. 2004, vol. 31, No. 1, pp. 29-35.

Schirmer et al. "Mouse models of IgG- and IgM-mediated hemolysis." Blood, vol. 109, No. 7, pp. 3099-3107, Apr. 2007.

Zupanska "Assays to predict the clinical significance of blood group antibodies." Current Opinion in Hemtaology, vol. 5, No. 6, Nov. 1998, pp. 412-416.

International Search Report PCT/US2010/053565 mailed Feb. 3, 2011.

Von Allmen et al., Development of a C1q-ABO-ELISA to meausre C1q binding by human anti-A alloantibodies. Journal of Immunological Methods 171: 85-92 (1994).

* cited by examiner

SYSTEMS AND METHODS FOR DETERMINING ANTIBODY-MEDIATED RISK INDEX

CROSS-REFERENCE TO RELATED APPLICATIONS

This application is a continuation-in-part of U.S. patent application Ser. No. 12/908,770, filed Oct. 20, 2010, now U.S. Pat. No. 8,426,210, issued on Apr. 23, 2013, which claims the benefit under 35 USC §119(e) to U.S. provisional application 61/253,774, filed Oct. 21, 2009, both of which are incorporated herein by reference in their entirety.

FIELD

Disclosed herein are systems and methods for assessing the antibody-mediated risk of neonatal alloimmune thrombocytopenic purpura, hemolytic disease of the fetus or neonate, and transfusion-related acute lung injury.

BACKGROUND

One of the more serious issues in medical practice is the difference in blood compatibility between mother and fetus or between patients and donor plasma. These incompatibilities can cause either a serious loss of functional fetal platelets or a severe anemia due to the destruction of fetal red blood cells, or acute lung injury in a patient which has been transfused with donor plasma containing antibodies to the HLA antigens of the recipient.

Hemolytic disease of the fetus or neonate (HDFN) is caused by the immunization of the mother to fetal red blood cell antigens during pregnancy, parturition, or abortion. The first-born child of the now immunized mother is not affected, however any subsequent pregnancy can result in severe anemia in the fetus or neonate due to maternal antibodies crossing through the placenta and destroying fetal red blood cells.

Neonatal alloimmune thrombocytopenic purpura (NAITP) is caused by the immune destruction of platelets in the fetus or neonate due to the presence of maternal antibodies. The result is a life-threatening thrombocytopenia that can cause intracranial bleeding and death in the undiagnosed fetus or neonate. Unlike HDFN, NAITP can occur in the first pregnancy as the immunization of the mother against fetal platelet antigens occurs due to the presence of fetal platelet antigens in the mother's circulation. Thus, the mother can produce antibodies during her pregnancy directed at the first child.

Transfusion-related acute lung injury (TRALI) is caused when antibodies present in whole blood, platelets, or plasma is transfused into a recipient who expresses those antigens on his immune cells. This can result in the accumulation of diffuse, patchy pulmonary densities with acute respiratory distress, chills, fever, and tachycardia. In a compromised patient, this reaction can be fatal.

The immune destruction of red blood cells, white blood cells, or platelets by antibodies is triggered by the activation of the complement cascade along with activation factors released from immune cells after binding with the offending antibody. Cells are burst by complement activation resulting in the release of hemoglobin into the patient's plasma (hemoglobinemia) or urine (hemoglobinuria) and can cause kidney damage due to fragments of destroyed cells being excreted through the kidney. Depending on the degree of hemolysis, the patient becomes anemic and can require additional transfusions of compatible red cells.

In general, the development of these immune antibodies is the result of transfusion or pregnancy. Only rarely are they are naturally occurring. When antibodies to red blood cells are first detected, all transfusions from that time forward must be shown to lack that specific antigen. The detection of antibodies to white blood cells or platelets is not normally performed until a transfusion reaction occurs, or an affected fetus or neonate is discovered after an immunized mother is identified. It is in this area where the probability of incompatibility may be unsuspected and an Antibody Mediated Risk Index (AMRI) will provide valuable information regarding the probability of transfusion or maternal-fetal risk.

The rate of immunization varies from one individual to another and studies have shown that approximately 1-2% of all transfused patients produce a specific alloantibody to a blood group antigen. These figures are much higher among patients who have received multiple transfusions, such as sickle cell anemia or leukemia patients, in which the patients develop an array of antibodies making the determination of blood transfusion compatibility much more difficult.

A person who has produced an antibody that is considered to be clinically significant is "sensitized" and must receive crossmatch-compatible blood. Cross-match compatibility is determined by mixing donor blood with the serum or plasma of the recipient and observing whether hemagglutination or hemolysis occurs. If either occurs, the blood is not transfused because of the possibility of causing a significant hemolytic event. Donor blood that is transfused must be shown to be antigen negative by testing with specific antisera. Thus, two tests must be performed to increase the safety of the pending blood transfusion While serologic tests can identify the presence of red blood cell-specific antibodies in human sera, similar tests for antibodies to platelets and white blood cells are not routinely performed unless there is an indication of the presence of offending antibodies. Furthermore, these assays cannot predict antibody-mediated risk.

SUMMARY

The disclosure provides systems, methods, and kits to predict the likelihood of an antibody-mediated event following a blood, platelet or plasma transfusion or as a result of pregnancy. The described systems, methods, and kits are useful to determine the Antibody-Mediated Risk Index ("AMRI"). The disclosed systems, methods, and kits provide for a much more rapid, efficient and less expensive method for evaluation of the antibody-mediated risk of neonatal alloimmune thrombocytopenic purpura, hemolytic disease of the fetus or neonate, and transfusion-related acute lung injury.

Thus, disclosed herein is a method of determining the risk of hemolytic disease of the fetus or neonate, neonatal alloimmune thrombocytopenic purpura, or transfusion-associated lung injury in a patient or transfusion recipient, the method comprising the steps of obtaining a sample of plasma or serum from the patient or transfusion recipient, optionally preparing an absorbed eluate of the sample; measuring the total immunoglobulin concentration in the sample or absorbed eluate of the sample, wherein the total immunoglobulin concentration is scored based on detection of a low immunoglobulin concentration, a medium immunoglobulin concentration, or a high immunoglobulin concentration, and the low immunoglobulin concentration is defined as a concentration less than 1:16 titer and is assigned zero points on the antibody-mediated risk index (AMRI), the medium immunoglobulin concentration is defined as a concentration range greater than 1:16 titer and less than 1:64 titer and is assigned 2 points on the AMRI, and the high immunoglobulin concentration is defined as a concentration greater than 1:64 titer and is assigned 10 points on the AMRI; measuring the antibody isotype of the immunoglobulins in the sample or absorbed eluate of the sample, wherein the immunoglobulin isotype is scored based on a presence of IgM, IgG1, IgG2, IgG3, or IgG4, and the presence of IgM is assigned 10 points on the AMRI, the presence of IgG1 is assigned 10 points on the AMRI, the presence of IgG2 is assigned 5 points on the AMRI, the presence of IgG3 is assigned 10 points on the AMRI, and the presence of IgG4 is assigned zero points on the AMRI; measuring the Fc gamma receptor affinity of the immunoglobulins in the sample or absorbed eluate of the sample, wherein the Fc gamma receptor affinity is scored based on detection of a Fcγ RI binding, a Fcγ RII binding, and/or a Fcγ RIII binding and detection of the Fcγ RI binding is assigned 10 points on the AMRI, detection of the Fcγ RII binding is assigned 2 points on the AMRI, and detection of the Fcγ RIII binding is assigned 5 points on the AMRI; measuring the C1q binding capacity of the immunoglobulins in the sample or absorbed eluate of the sample, wherein C1q binding capacity is scored based on detection of a low C1q binding (less than 0.49) or a high C1q binding (0.5 or higher), and the low C1q binding is assigned 2 points on the AMRI and the high C1q binding is assigned 10 points on the AMRI; and calculating the AMRI based on the measurements of total immunoglobulin concentration, antibody isotype of the immunoglobulins, Fc gamma receptor affinity of the immunoglobulins, and C1q binding capacity of the immunoglobulins and thereby determining the risk of hemolytic disease of the fetus or neonate, neonatal alloimmune thrombocytopenic purpura, or transfusion-associated lung injury in a patient or transfusion recipient, wherein the AMRI is the sum of total points accrued.

In one embodiment, an AMRI of about 30 or higher indicates a high risk, an AMRI of about 15 to 30 indicates a moderate risk, and AMRI of about 15 or lower indicates a low risk.

In another embodiment, the AMRI determines risk of hemolytic disease of the fetus or neonate, risk of neonatal alloimmune thrombocytopenic purpura, or risk of transfusion-associated lung injury.

Also disclosed herein is an assay for predicting the risk of hemolytic disease of the fetus or neonate, neonatal alloimmune thrombocytopenic purpura, or transfusion-associated lung injury in a patient or transfusion recipient comprising measuring (i) the total immunoglobulin concentration of a sample of serum, plasma or absorbed eluate of the sample, wherein the total immunoglobulin concentration is scored based on detection of a low immunoglobulin concentration, a medium immunoglobulin concentration, or a high immunoglobulin concentration, and the low immunoglobulin concentration is defined as a concentration less than 1:16 titer and is assigned zero points on the AMRI, the medium immunoglobulin concentration is defined as a concentration range greater than 1:16 titer and less than 1:64 titer and is assigned 2 points on the AMRI, and the high immunoglobulin concentration is defined as a concentration greater than 1:64 titer and is assigned 10 points on the AMRI, (ii) the isotype of the immunoglobulins in the sample, wherein the immunoglobulin isotype is scored based on a presence of IgM, IgG1, IgG2, IgG3, or IgG4, and the presence of IgM is assigned 10 points on the AMRI, the presence of IgG1 is assigned 10 points on the AMRI, the presence of IgG2 is assigned 5 points on the AMRI, the presence of IgG3 is assigned 10 points on the AMRI, and the presence of IgG4 is assigned zero points on the AMRI, (iii) the Fc gamma receptor affinity of the immunoglobulins in the sample, wherein determination of the Fc gamma receptor affinity is scored based on detection of a Fcγ RI binding, a Fcγ RII binding, and/or a Fcγ RIII binding and detection of the Fcγ RI binding is assigned 10 points on the AMRI, detection of the Fcγ RII binding is assigned 2 points on the AMRI, and detection of the Fcγ RIII binding is assigned 5 points on the AMRI, and (iv) the C1q complement binding capacity of the immunoglobulins in the sample, wherein C1q binding capacity is scored based on detection of a low C1q binding (less than 0.49) or a high C1q binding (0.5 or higher), and the low C1q binding is assigned 2 points on the AMRI and the high C1q binding is assigned 10 points on the AMRI; and calculating a AMRI based on the measurements of total immunoglobulin concentration, antibody isotype of the immunoglobulins, Fc gamma receptor affinity of the immunoglobulins, and C1q binding capacity of the immunoglobulins wherein the relative hemolytic index predicts the risk of hemolytic disease of the fetus or neonate, neonatal alloimmune thrombocytopenic purpura, or transfusion-associated lung injury in a patient or transfusion recipient, wherein the AMRI is the sum of total points accrued. In another embodiment, the AMRI is calculated using a specific algorithm.

In one embodiment, an AMRI of about 30 or higher indicates a high risk, an AMRI of about 15 to 30 indicates a moderate risk, and AMRI of about 15 or lower indicates a low risk.

In another embodiment, the AMRI determines risk of hemolytic disease of the fetus or neonate, risk of neonatal alloimmune thrombocytopenic purpura, or risk of transfusion-associated lung injury.

In another embodiment, the sample is whole blood, serum, plasma, or an eluate thereof. In another embodiment, the sample comprises an absorbed eluate of plasma or serum from the patient or transfusion recipient. In yet another embodiment, the immunoglobulin concentration is an immunoglobulin titer.

DETAILED DESCRIPTION

The disclosure provides improved methods for determining the likelihood of antibody-mediated hemolytic or autoimmune events as a result of transfusion or other blood exposure (for example between the mother and fetus or neonate) that results in neonatal alloimmune thrombocytopenic purpura, hemolytic disease of the fetus or neonate, or transfusion-related acute lung injury. The disclosed methods are highly accurate as well as time and cost efficient.

The plasma molecules that promote hemolysis are referred to as immunoglobulins (Ig) or antibodies. Immunoglobulins are principally responsible for the detection and elimination of foreign antigens whether they are bacteria, toxins, proteins, carbohydrates or transfused cells. Once the immune system has responded to a particular antigen, any additional exposure to the same antigen causes a rapid secondary, or anamnestic response, resulting in a much higher titer of Igs in the serum.

Human Igs are classified into the following isotypes: IgG1, IgG2, IgG3, IgG4, IgA, secretory IgA, IgM, IgE and IgD.

Immunoglobulin G (IgG) is by far the most prevalent serum antibody in normal human samples accounting for approximately 75% of the total mean serum Ig concentration.

The basic structure of the Ig molecule is two light chains, either κ (kappa) or λ (lambda), linked by disulfide bonds to two heavy chains of either of the 5 immunoglobulin classes (IgA, IgD, IgE, IgG and IgM) in the configuration of a monomer, dimer, trimer, quadrimer or pentamer. Each class differs in serum concentration, molecular weight, serum half-life, ability to bind complement (a set of plasma proteins that act together to attack extracellular pathogens), active placental transfer, and binding properties to various proteins.

Certain Ig characteristics are known to increase the risk of hemolytic disease of the fetus or neonate (HDFN), neonatal alloimmmune thrombocytopenic purpura (NAITP), and transfusion-related acute lung injury (TRALI). These characteristics include total Ig concentration, Ig isotype, and ability to bind C1q to activate complement and/or Fc gamma receptor (FcγR) affinity.

Figure 1:
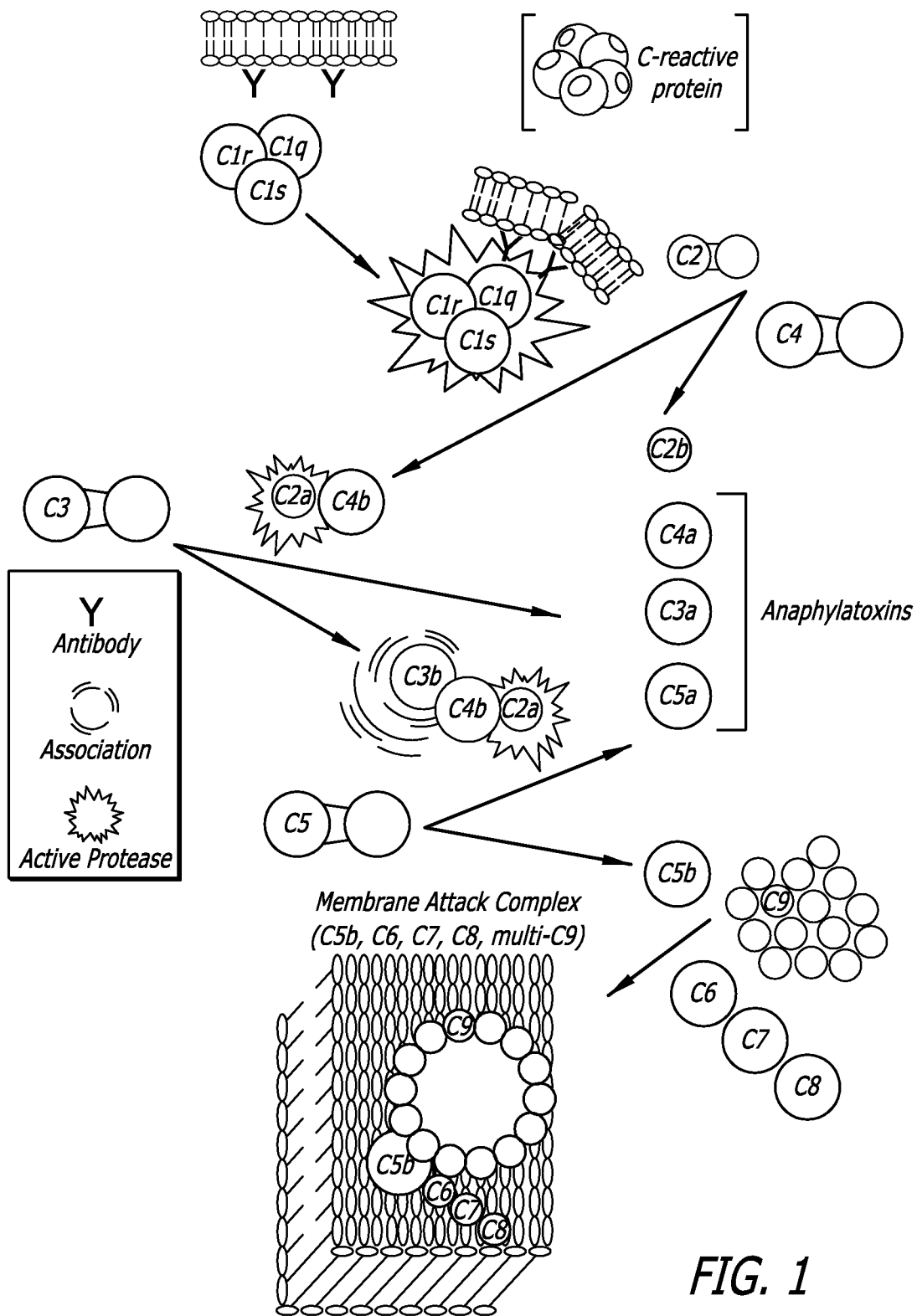
FIG. 1 depicts the complement activation pathway.

The classical pathway of complement activation (FIG. 1) starts with C1, a complex of serine proteases C1r and C1s (two each), and six larger C1q glycoproteins. Activation occurs by the binding of C1q to the Fc binding domains of IgG or IgM after they become attached to a target antigen. At least two of the N-terminal portions of C1q must be bound for C1 activation. It is the CH2 domain of the Fc receptor which is required for C1q binding. Three amino acid residues, Glu318, Lys320 and Lys322, have been found to be conserved in human IgG and in Igs from several other species, thus they have been designated as the C1q binding motif. However, further differences exist between the isotype core binding sites. The possibility exists, therefore, that these differences can determine the potential of an antibody, whether an alloantibody or an autoantibody, to cause decreased likelihood of transfused red cell survival or neonatal alloimmune thrombocytopenic purpura, hemolytic disease of the fetus or neonate, or transfusion-related acute lung injury.

The foregoing suggests that Igs efficient at binding C1q can more readily activate complement. It is known that IgM antibodies activate complement more efficiently than IgG antibodies. While isotypes IgG1, IgG2 and IgG3 can activate complement to varying degrees, IgG4 and IgA do not and thus are less likely to cause neonatal alloimmune thrombocytopenic purpura, hemolytic disease of the fetus or neonate, or transfusion-related acute lung injury.

Immunoglobulins binding FcγRs are also involved in the occurrence of neonatal alloimmune thrombocytopenic purpura, hemolytic disease of the fetus or neonate, or transfusion-related acute lung injury. Human FcγRs are expressed on the surface of immune cells (monocytes, macrophages, neutrophils, dendritic cells, NK cells, etc.). Each FcγR has different extracellular and intracellular domains, complicated by some having polymorphic extracellular domains. This includes high and low affinity members, all of which can bind to IgG immune complexes, but only high affinity receptors can bind to monomeric IgG. In humans, there is one high affinity receptor, FcγRI (CD64), and there are two families (FcγRII and FcγRIII) of low affinity IgG receptors comprising FcγRIIa (CD32a), FcγRIIb (CD32b), FcγRIIc (CD32c), FcγRIIIa (CD16a) and FcγRIIIb (CD16b). The term CD refers to cluster of differentiation or designation and refers to a specific antigen on a cell surface. FcRI, FcRIIa, FcRIIc and FcRIIIa are activating receptors. FcRIIb is an inhibitory receptor, and FcRIIIb is a GPI-linked receptor of uncertain function. FcγRI has three extracellular immunoglobulin (Ig)-like domains, one more domain than members of the FcγRII and FcγRIII families, thereby allowing direct activation by the binding of a monomeric antibody, rather than a complexed dimeric antibody such as with FcγRII and FcγRIII. FcγR binding initiates immune responses such as cytokine production, phagocytosis and serotonin release.

The glycosylation of the IgG antibody maintains the structure needed for C1q binding and FcγR affinity. It is thought that de-glycosylated IgG antibodies are unable to regulate in vivo activated inflammatory responses. Altered IgG glycosylation has been found in many autoimmune diseases such as rheumatoid arthritis and autoimmune thrombocytopenia where the antibodies are primarily de-glycosylated when compared to those from normal controls. The level of glycosylation has also been shown to vary with the process of aging and with immunization events, such as a blood transfusion and pregnancy. Accordingly, antibody glycosylation is a factor to consider in assessing the risk of hemolysis.

Figure 2:
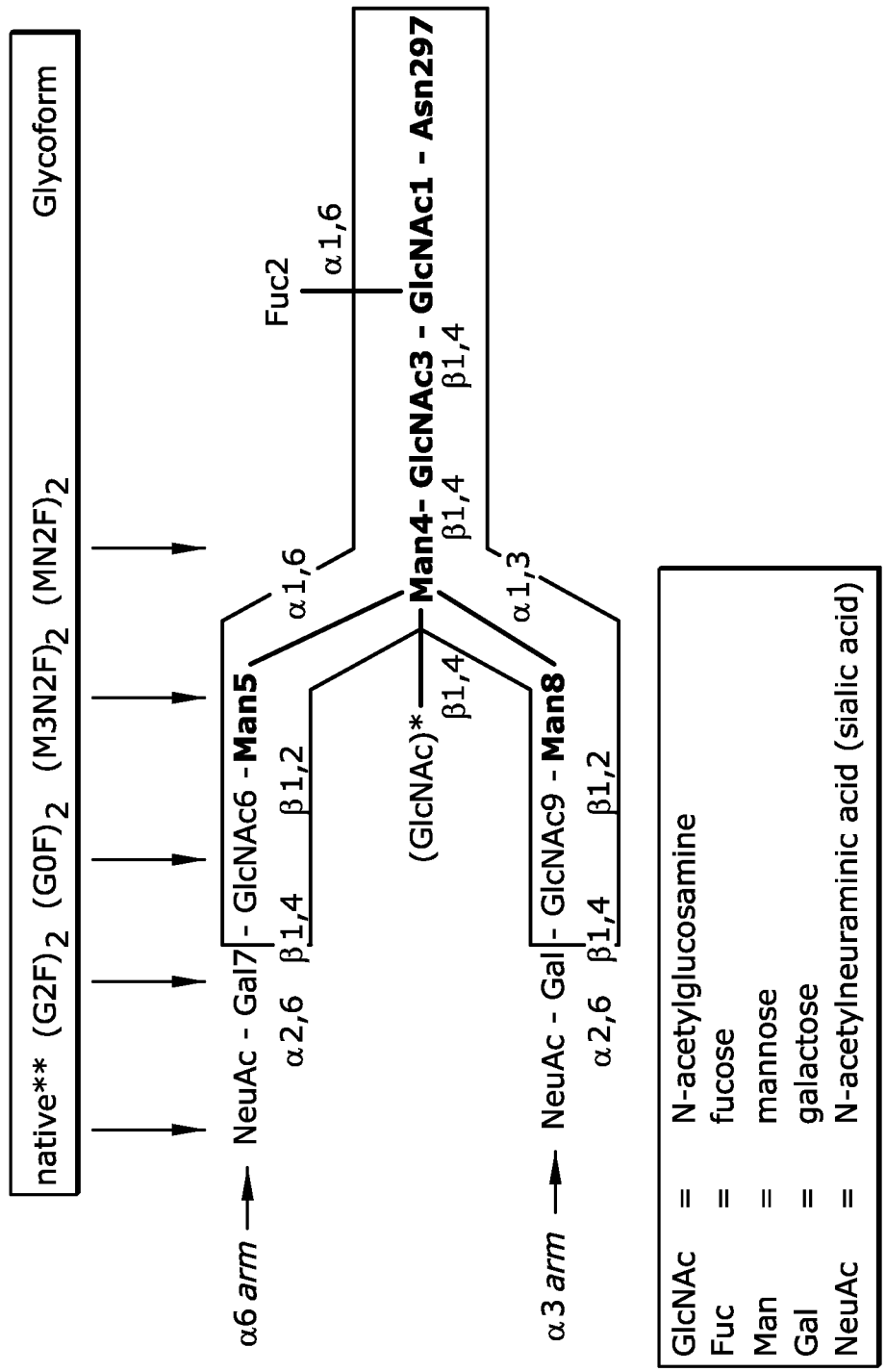
FIG. 2 depicts the carbohydrate sequence linked to Asn297 of human IgG1-Fc.

The N-linked glycan at Asn297 of the Fc receptor is alternatively glycosylated with fucose, galactose and terminal sialic acid at different time points. FIG. 2 depicts the carbohydrate sequence linked to Asn297 of human IgG1-Fc. The effects of alternative glycosylation can be determined by treating antibodies with PNGase F which cleaves between the innermost GlcNAc residue and the Asp297 residues of high mannose and complex oligosaccharides from the N-linked glycoproteins. Alternatively, treatment with neuraminidase can selectively hydrolyze α-(2→3), α-(2→6), α-(2→8) and/or α-(2-9) linked NeuAc residues from complex oligosaccharides, depending on the source of the terminal residues. De-glycosylated and de-sialylated antibodies can then be tested for altered binding activity to C1q and FcγRs.

The currently disclosed Antibody-Mediated Risk Index (AMRI) assay utilizes all of these factors in predicting the risk of HDFN, NAITP, or TRALI. Particularly, the AMRI assay evaluates total IgG immunoglobulin concentration (or titer) and IgG/A/M isotype, C1q complement binding capacity, and FcγR affinity. By offering these tests in a multiplex assay, the AMRI methods described herein can provide much needed laboratory data to predict a particular patient's AMRI—that is, the likelihood for any particular patient antibody to cause a severe reaction, that is, decreased survival of transfused red cells and/or in vivo hemolysis of red blood cells, destruction of platelets, or acute lung injury. The described AMRI methods also offer the following advantages: ability to use sample size as small as about 200 μL; ability to use hemolyzed samples; ability to use whole blood, serum or plasma on RBC elutions of each antibody; insensitivity to sample age; speed (i.e. several hours vs. several days); cost effectiveness; multiplex format; and accuracy.

Samples submitted for AMRI evaluation can be serum, plasma, or an eluate, which is an absorbed and purified preparation of the antibody.

For C1q binding, ELISA plates (BD Falcon, Franklin Lakes, N.J.) are first coated with 10 ng purified C1q protein (Sigma, St. Louis, Mo.) and left overnight at 4° C. After blocking (SuperBlock, Pierce, Rockford Ill.) for 2 hr at room temperature (RT), the plates are washed twice (1% Tween-20 in PBS pH 7.3, Sigma) and 100 μl antibody added and incubated for 1 hr at RT. After three washings, 100 μl HRP-conjugated anti-IgG is added and the plate again incubated for 1 hour. After three final washings, the color is developed by the addition of 50 μl TMB substrate with $H_2O_2$ and allowed to develop for 10 min. The reaction is then stopped by the addition of 50 μl 1N $H_2SO_4$ and the plate OD read at 450 nm. The results are shown below in Table 1 (total Ig Concentration, IgG/M Isotype and C1q Binding (IAT=Indirect Antiglobulin Test—the strength of hemagglutination scored from negative or 0 to a maximum positive of 12)).

TABLE 1

| Sample # | | 1 | 2 | 3 | 4 | 5 | 6 | 7 | 8 | 9 | 10 |
|---|---|---|---|---|---|---|---|---|---|---|---|
| IAT | score | 12 | 10 | 11 | 11 | 10 | 11 | 11 | 9 | 7 | 10 |
| Total IgG | ng/ml | 6667 | 1313 | 610 | 2668 | 100 | 7116 | 1287 | 1853 | 2368 | 1701 |
| IgG1 | | 2031 | 310 | 398 | 1888 | 15 | 2771 | 221 | 893 | 763 | 398 |
| IgG2 | | 2266 | 0 | 0 | 0 | 66 | 0 | 111 | 0 | 118 | 87 |
| IgG3 | | 1026 | 53 | 50 | 235 | 41 | 608 | 144 | 179 | 467 | 46 |
| IgG4 | | 27 | 0 | 0 | 0 | 2 | 0 | 11 | 0 | 0 | 0 |
| IgM | | 0 | 0 | 0 | 0 | 0 | 0 | 0 | 0 | 0 | 0 |
| Total Sum | | 5350 | 363 | 448 | 2123 | 124 | 3379 | 487 | 1072 | 1348 | 531 |
| C1q Binding | | POS | Neg | Neg | POS | Neg | Neg | Neg | POS | POS | Neg |
| Elisa Assay Blank | | .083 .1377 | .7319 .7502 | .1273 .2998 | .1377 .2261 | .6871 .7779 | .1393 .1684 | .1397 .1954 | .1289 .1476 | .5402 .6227 | .6778 .6754 | .1199 .1423 |

Similar ELISA methods were developed for measuring the total IgG concentration as well as the isotype of the immunoglobulins (IgG1, IgG2, IgG3, IgG, IgM and IgA) and Fcγ receptor affinity (FcγRI, FcγRIIa and FcγRIIIa). Briefly, proteins specific for human Ig isotypes IgG1, IgG2, IgG3, IgG4, IgM, and IgA, or activating Fc receptor FcγRI, FcγRIIa, and FcγRIIIa, were each were coated on 96-well ELISA plates. Each method was validated by multiple assays and standardized using commercially available controls for each protein being assayed.

The results of the total IgG and the isotype testing are compared to the results from the C1q binding by ELISA (Table 1). As can be seen in samples 1, 4, 8 and 9, these samples have higher IgG concentrations. These high IgG1, IgG2 and IgG3 with a high C1q binding affinity will predict a positive monocyte monolayer assay (MMA). FcγR affinity to receptors I and IIIa provide additional evidence for in vivo antibody-mediated events.

Table 2 below depicts an example of calculation of a relative hemolytic index (RHI) which uses the same algorithm in FIG. 3 to determine risk of hemolytic events in blood transfusions as disclosed in co-pending U.S. patent application Ser. No. 12/908,770, which is incorporated by reference for all it discloses regarding RHI. The RHI values are obtained with antibodies to red blood cell antigens. Similar values will be obtained for the AMRI for samples relevant to HDFN, NAITP, and TRALI.

TABLE 2

| RHI Assay | Mab Anti-D 7E11 | RHI Score | Mab Anti-D 10D6 | RHI Score | Human Anti-c | RHI Score | Human Anti- D + C | RHI Score | Human Warm/ Cold Mixed Auto | RHI Score |
|---|---|---|---|---|---|---|---|---|---|---|
| Total IgG | 1:1024 | 10 | 1:1024 | 10 | 1:2 | 0 | 1:2048 | 10 | 1:64 | 2 |
| IgG Isotype | IgG1 | 10 | IgG1 | 10 | IgG1 | 10 | IgG1 | 10 | IgG1 | 10 |
| | IgG2 | | IgG2 | | IgG2 | 5 | IgG2 | 5 | IgG2 | 0 |
| | IgG3 | | IgG3 | | IgG3 | 10 | IgG3 | 10 | IgG3 | 10 |
| | IgG4 | | IgG4 | | IgG4 | 0 | IgG4 | 0 | IgG4 | 0 |
| | IgM | | IgM | | IgM | | IgM | | IgM | 10 |
| C1q Binding | 0.26 | 2 | 1.47 | 10 | 0.68 | 10 | 0.54 | 10 | 0.38 | 2 |
| Fc gamma Receptor Affinity | I IIa IIIa | 10 2 5 | I IIa IIIa | 10 2 5 | I IIa IIIa | 0 2 0 | I IIa IIIa | 10 2 0 | I IIa IIIa | 10 2 0 |
| Total RHI * | | 39 | | 47 | | 27 | | 57 | | 46 |
| Interpretation | | Significant | | Significant | | Not Significant | | Significant | | Significant |
| % MMA ** | | 30.5% | | 44% | | 0.25% | | 47.5% | | 12.2% |

* RHI over 35 considered significant
** Total MMA over 5% considered significant levels indicate samples more likely to contain reactive antibodies. Samples with a generally lower total IgG concentration do not produce a very strong signal for C1q binding.

Figure 3:
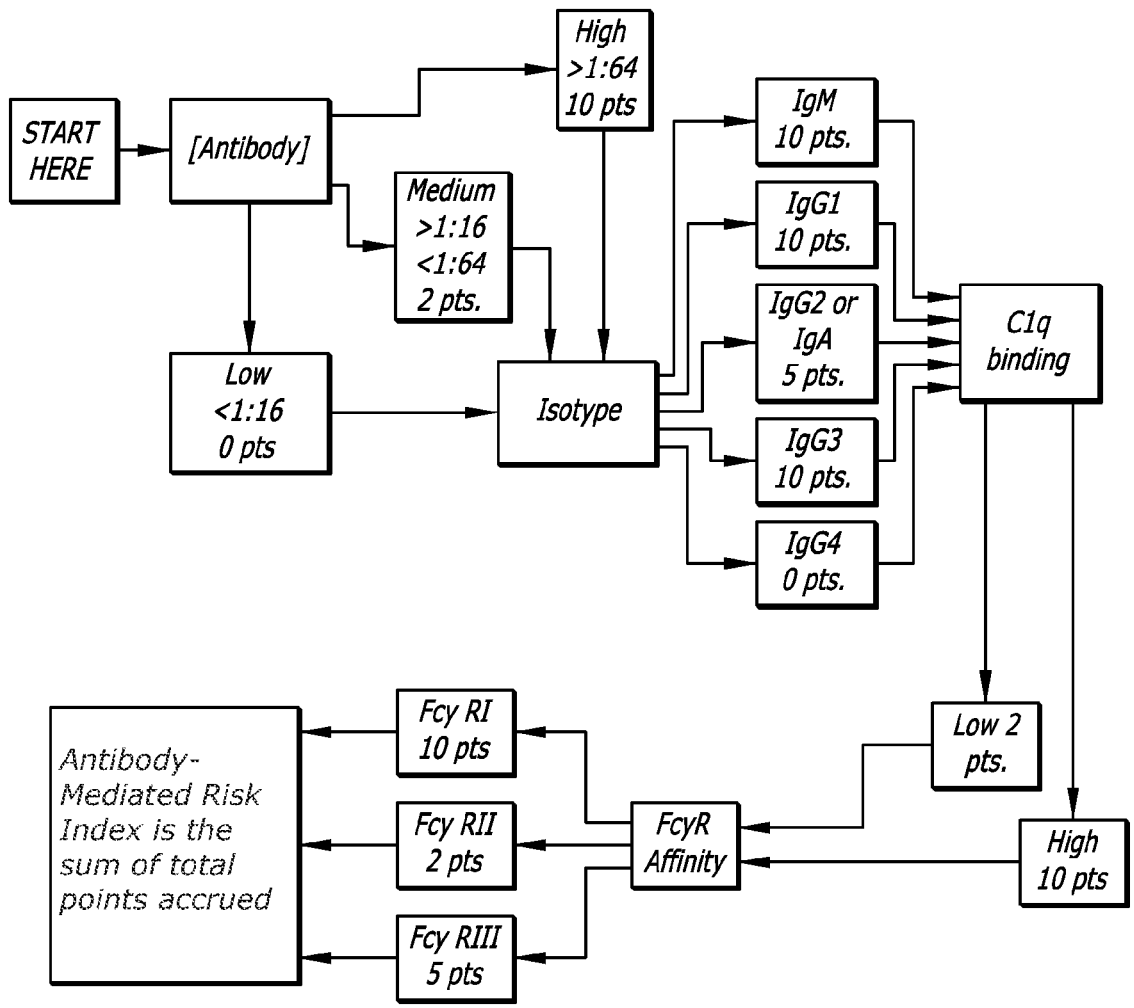
FIG. 3 is a flow chart of steps to establish a antibody-mediated risk index score in accordance with an embodiment disclosed herein.

FIG. 3 provides a flow chart for the determination of a AMRI as disclosed herein. In this example flow chart, if a sample is IgG4 of low titer, did not require C1q testing and did not have any FcγR affinity, the AMRI is zero. However, if a sample is of a high titer IgG1, it would be further evaluated, and with a high C1q binding and FcγRI affinity, this sample achieved an AMRI of 40, thus it is likely to cause in vivo hemolysis. Antibodies of high concentration and isotype The % MMA cutoff value of 5% has been shown to indicate the probability of a significant reaction due to the presence of antibodies to red blood cell antigens.

The range for the AMRI is between 15 or below and over 30 or higher. Greater than 30 is a high risk (or significant) of reaction, while anything below 15 is considered to be low (insignificant) risk of reaction. The AMRI is calculated by the number of points each sample earns in the various tests. Adding the total points earned for Ig concentration, isotype presents (or predominant), C1q binding capacity (high or low) and affinity for each Fc gamma receptor on immune cells (I, IIa, IIIa) provides the score for the AMRI. The significance of the AMRI score is similar to that of RHI.

By establishing newer methods for the study of immunoglobulins, namely as risk assessment tool in multiplex format, the AMRI has been developed to predict risk of HDFN, NAITP, and TRALI. The AMRI replaces the standard bioassays which are currently used to predict HDFN, the chemoluminescence test, the antibody dependant cellular cytotoxicity assay (ADCC), the monocyte monolayer assay (MMA), and $^{51}$Cr RBC survival studies. The AMRI is designed to be both a cost and time efficient tool for patient transfusion management. This test can be offered to the clinician worried about patient morbidity due either to allo- or auto-antibodies. Including sample preparation, the AMRI analysis can be completed within about 2 to about 4 hours, in contrast to the existing bioassays that require special skills, equipment and planning often takes days or even weeks to obtain results.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of determining the risk of hemolytic disease of the fetus or neonate, neonatal alloimmune thrombocytopenic purpura, or transfusion-associated lung injury in a patient or transfusion recipient, the method comprising the steps of:

obtaining a sample of plasma or serum from the patient or transfusion recipient;

optionally preparing an absorbed eluate of the sample;

measuring the total immunoglobulin concentration in the sample or absorbed eluate of the sample, wherein the total immunoglobulin concentration is scored based on detection of a low immunoglobulin concentration, a medium immunoglobulin concentration, or a high immunoglobulin concentration, and the low immunoglobulin concentration is defined as a concentration less than 1:16 titer and is assigned zero points on the antibody-mediated risk index (AMRI), the medium immunoglobulin concentration is defined as a concentration range greater than 1:16 titer and less than 1:64 titer and is assigned 2 points on the AMRI, and the high immunoglobulin concentration is defined as a concentration greater than 1:64 titer and is assigned 10 points on the AMRI;

measuring the antibody isotype of the immunoglobulins in the sample or absorbed eluate of the sample, wherein the immunoglobulin isotype is scored based on a presence of IgM, IgG1, IgG2, IgG3, or IgG4, and the presence of IgM is assigned 10 points on the AMRI, the presence of IgG1 is assigned 10 points on the AMRI, the presence of IgG2 is assigned 5 points on the AMRI, the presence of IgG3 is assigned 10 points on the AMRI, and the presence of IgG4 is assigned zero points on the AMRI;

measuring the Fc gamma receptor affinity of the immunoglobulins in the sample or absorbed eluate of the sample, wherein the Fc gamma receptor affinity is scored based on detection of an Fcγ RI binding, an Fcγ RII binding, and/or an Fcγ RIII binding, and detection of the Fcγ RI binding is assigned 10 points on the AMRI, detection of the Fcγ RII binding is assigned 2 points on the AMRI, and detection of the Fcγ RIII binding is assigned 5 points on the AMRI;

measuring the C1q binding capacity of the immunoglobulins in the sample or absorbed eluate of the sample, wherein C1q binding capacity is scored based on detection of a low C1q binding (less than 0.49) or a high C1q binding (0.5 or higher), and the low C1q binding is assigned 2 points on the AMRI and the high C1q binding is assigned 10 points on the AMRI; and calculating the AMRI by adding the points obtained from measurements of total immunoglobulin concentration, antibody isotype of the immunoglobulins, Fc gamma receptor affinity of the immunoglobulins, and C1q binding capacity of the immunoglobulins;

wherein the AMRI is indicative of the risk of hemolytic disease of the fetus or neonate, neonatal alloimmune thrombocytopenic purpura, or transfusion-associated lung injury in a patient or transfusion recipient.

2. The method of claim 1, wherein an AMRI of about 30 or higher indicates a high risk.

3. The method of claim 1, wherein an AMRI of about 15 to 30 indicates a moderate risk.

4. The method of claim 1, wherein an AMRI of about 15 or lower indicates a low risk.

5. The method of claim 1, wherein the AMRI determines risk of hemolytic disease of the fetus or neonate.

6. The method of claim 1, wherein the AMRI determines risk of neonatal alloimmune thrombocytopenic purpura.

7. The method of claim 1, wherein the AMRI determines risk of transfusion-associated lung injury.

8. An assay for predicting the risk of hemolytic disease of the fetus or neonate, neonatal alloimmune thrombocytopenic purpura, or transfusion-associated lung injury in a patient or transfusion recipient comprising measuring:

(i) the total immunoglobulin concentration of a sample of serum, plasma, or absorbed eluate of the sample, wherein the total immunoglobulin concentration is scored based on detection of a low immunoglobulin concentration, a medium immunoglobulin concentration, or a high immunoglobulin concentration, and the low immunoglobulin concentration is defined as a concentration less than 1:16 titer and is assigned zero points on the antibody-mediated risk index (AMRI), the medium immunoglobulin concentration is defined as a concentration range greater than 1:16 titer and less than 1:64 titer and is assigned 2 points on the AMRI, and the high immunoglobulin concentration is defined as a concentration greater than 1:64 titer and is assigned 10 points on the AMRI, (ii) the isotype of the immunoglobulins in the sample, wherein the immunoglobulin isotype is scored based on a presence of IgM, IgG1, IgG2, IgG3, or IgG4, and the presence of IgM is assigned 10 points on the AMRI, the presence of IgG1 is assigned 10 points on the AMRI, the presence of IgG2 is assigned 5 points on the AMRI, the presence of IgG3 is assigned 10 points on the AMRI, and the presence of IgG4 is assigned zero points on the AMRI, (iii) the Fc gamma receptor (Fcγ R) affinity of the immunoglobulins in the sample, wherein determination of the Fc gamma receptor affinity is scored based on detection of an Fcγ RI binding, an Fcγ RII binding, and/or an Fcγ RIII binding, and detection of the Fcγ RI binding is assigned 10 points on the AMRI, detection of the Fcγ RII binding is assigned 2 points on the AMRI, and detection of the Fcγ RIII binding is assigned 5 points on the AMRI, and (iv) the C1q complement binding capacity of the immunoglobulins in the sample, wherein C1q binding capacity is scored based on detection of a low C1q binding (less than 0.49) or a high C1q binding (0.5 or higher), and the low C1q binding is assigned 2 points on the AMRI, and the high C1q binding is assigned 10 points on the AMRI; and calculating an AMRI by adding the points obtained from measurements of total immunoglobulin concentration, antibody isotype of the immunoglobulins, Fc gamma receptor affinity of the immunoglobulins, and C1q binding capacity of the immunoglobulins;

wherein the AMRI is indicative of the risk of hemolytic disease of the fetus or neonate, neonatal alloimmune thrombocytopenic purpura, or transfusion-associated lung injury in a patient or transfusion recipient.

9. The assay of claim 8, wherein the AMRI is calculated using a specific algorithm.

10. The assay of claim 8, wherein an AMRI of about 30 or higher indicates a high risk.

11. The assay of claim 8, wherein an AMRI of about 15 to 30 indicates a moderate risk.

12. The assay of claim 8, wherein an AMRI of about 15 or lower indicates a low risk.

13. The assay of claim 8, wherein the sample is whole blood, serum, plasma, or an eluate thereof.

14. The assay of claim 8, wherein the sample comprises an absorbed eluate of plasma or serum from the patient or transfusion recipient.

15. The assay of claim 8, wherein the immunoglobulin concentration is an immunoglobulin titer.

16. The assay of claim 8, wherein the AMRI determines risk of hemolytic disease of the fetus or neonate.

17. The assay of claim 8, wherein the AMRI determines risk of neonatal alloimmune thrombocytopenic purpura.

18. The assay of claim 8, wherein the AMRI determines risk of transfusion-associated lung injury.

19. A method of determining the risk of hemolytic disease of the fetus or neonate, neonatal alloimmune thrombocytopenic purpura, or transfusion-associated lung injury in a patient or transfusion recipient comprising performing the assay of claim 8 and obtaining an AMRI which is indicative of the risk of hemolytic disease of the fetus or neonate, neonatal alloimmune thrombocytopenic purpura, or transfusion-associated lung injury in a patient or transfusion recipient.

* * * * *